(12) United States Patent
Heilek et al.

(10) Patent No.: US 10,173,147 B2
(45) Date of Patent: Jan. 8, 2019

(54) APPARATUS AND PROCESS FOR SEPARATING A TARGET PRODUCT FROM A LIQUID PHASE COMPRISING THE TARGET PRODUCT

(71) Applicant: BASF SE, Ludwigshafen (DE)

(72) Inventors: Joerg Heilek, Bammental (DE); Rainer Askani, Mannheim (DE); Ulrich Hammon, Mannheim (DE); Wolfgang Schneider, Bad Duerkheim (DE); Thomas Walter, Hassloch (DE)

(73) Assignee: BASF SE, Ludwigshafen (DE)

( * ) Notice: Subject to any disclaimer, the term of this patent is extended or adjusted under 35 U.S.C. 154(b) by 323 days.

(21) Appl. No.: 14/738,033

(22) Filed: Jun. 12, 2015

(65) Prior Publication Data

US 2015/0360142 A1   Dec. 17, 2015

Related U.S. Application Data

(60) Provisional application No. 62/011,068, filed on Jun. 12, 2014.

(30) Foreign Application Priority Data

Jun. 12, 2014   (DE) .................... 10 2014 108 275

(51) Int. Cl.
*B01D 9/00*   (2006.01)
*C07C 51/43*   (2006.01)

(52) U.S. Cl.
CPC ........... *B01D 9/0004* (2013.01); *B01D 9/005* (2013.01); *B01D 9/0013* (2013.01); *C07C 51/43* (2013.01)

(58) Field of Classification Search
CPC .... B01D 9/0004; B01D 9/0013; B01D 9/005; C07C 51/43
See application file for complete search history.

(56) References Cited

U.S. PATENT DOCUMENTS 3,272,875 A * 9/1966 Gordon ................ B01D 9/0013
                                                159/13.3
3,377,134 A * 4/1968 Baker ........................ B01J 2/30
                                                159/16.1

(Continued)

FOREIGN PATENT DOCUMENTS

DE          103 32 758 A1     5/2004
DE   10 2007 004 960 A1      7/2008

(Continued)

OTHER PUBLICATIONS

Alfa Laval AlfaDisc Plate and Shell Heat Exchanger, uploaded by Scott Sobolewski. Published Aug. 14, 2009. https://youtu.be/RPdaYXIsrE.*

(Continued)

*Primary Examiner* — Youngsul Jeong
(74) *Attorney, Agent, or Firm* — Oblon, McClelland, Maier & Neustadt, L.L.P.

(57) ABSTRACT

The present invention relates to an apparatus (1) for separation of a target product from a liquid phase P comprising the target product, comprising
  at least one primary space (3) for a heat transfer medium W,
  at least one first feed unit (5a) and one first removal unit (5b) for the heat transfer medium W,
  at least one secondary space (7) for the liquid phase P,
  at least one second feed unit (9) for the liquid phase P,
  at least one crystallization surface (13) which divides the primary space (3) and the secondary space (7),
  at least one second removal unit (15) for the target product and
  at least one application unit (11) for a liquid phase $P_0$ essentially directly to the crystallization surface (13) or the surfaces of lines that conduct the heat transfer medium W.

Figure 1:
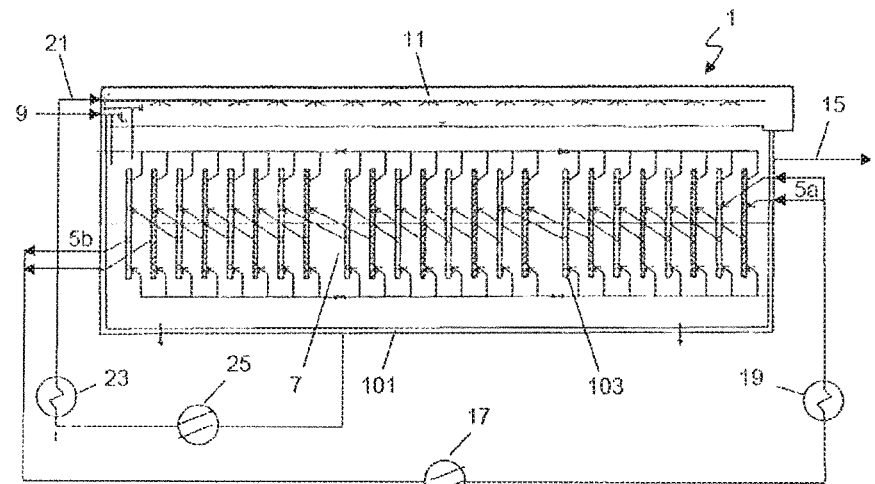

The present invention further relates to a process for removing a target product from a liquid phase P comprising the target product.

5 Claims, 1 Drawing Sheet

(56) References Cited

U.S. PATENT DOCUMENTS

| | | | | |
|---|---|---|---|---|
| 4,486,395 | A | * | 12/1984 | Witte .................. B01D 9/0013 127/16 |
| 4,507,244 | A | * | 3/1985 | von Rappard ....... B01D 9/0022 23/299 |
| 2005/0090628 | A1 | | 4/2005 | Eck et al. |
| 2008/0183014 | A1 | | 7/2008 | Diefenbacher et al. |
| 2009/0076284 | A1 | | 3/2009 | Heilek et al. |
| 2009/0076286 | A1 | | 3/2009 | Heilek et al. |

FOREIGN PATENT DOCUMENTS

| | | |
|---|---|---|
| DE | 10 2007 043 748 A1 | 9/2008 |
| DE | 10 2007 043 759 A1 | 9/2008 |
| DE | 10 2007 043 758 A1 | 10/2008 |

OTHER PUBLICATIONS

Process Equipment Solutions, 2012, AlfaDisc, All-welded Plate Heat Exchanger, http://www.pesllconline.com/wpcontent/uploads/2012/03/AlfaDisc.pdf.*

Tranter, 2013, Heat Exchangers, Product Literature Welded, https://www.fernstrum.com/wp-content/uploads/2013/08/Welded-Products-Brochure.pdf.*

AlfaDisc 2012 screencapture from Google search.*

U.S. Appl. No. 14/737,025, filed Jun. 11, 2015, Hammon, et al.

* cited by examiner

APPARATUS AND PROCESS FOR SEPARATING A TARGET PRODUCT FROM A LIQUID PHASE COMPRISING THE TARGET PRODUCT

This patent application claims the benefit of U.S. provisional patent application Ser. No. 62/011,068 and DE patent application Serial Number DE 102014108275.3, both filed on Jun. 12, 2014, incorporated in their entirety herein by reference.

The present invention relates to an apparatus and to a process for separating a target product from a liquid phase P comprising the target product and by-products.

Apparatuses and processes of the same generic type for separating a target product from a liquid phase P with the aid of an indirect heat transferer having a secondary space and a primary space are known per se, for example from DE 103 32 758 A1 or DE 10 2007 004 960 A1.

As a result of the transfer of heat in the liquid phase P supplied to the secondary space through the wall dividing a secondary space and a primary space from one another (i.e. a heat transfer surface) into the cooling medium flowing within the primary space, the liquid phase P is cooled down until the saturation limit of the target product in the liquid phase P is exceeded and the saturation is counteracted by formation of crystals of the target product.

Crystallizative removal of a target product is employed especially in order to separate this target product from by-products formed in the course of preparation thereof. In this case, the target product may already have been prepared directly by chemical reaction in the liquid phase. However, the target product may also have been prepared, for example, in the gas phase, from which the target product is subsequently converted to liquid phase, generally by condensative and/or absorptive measures, normally together with some of the secondary components that accompany the target product in the gas phase.

The crystallizative removal of the target product can be effected as a "sharp" thermal separation process, in principle directly from the liquid phase P containing target product and by-products that arises in the course of preparation of the target product. However, it has become standard practice to first of all subject the aforementioned liquid phase to at least one "nonsharp" thermal separation process for the purpose of separating a portion of the aforementioned by-products and secondary components from the target product.

A "nonsharp" separation process refers to one in which, from a thermodynamic point of view, the composition which arises on employment of the separation process with the target product is dependent in a thermodynamically obligatory manner on the composition of the mixture to be subjected to the separation process. The "nonsharp" thermal separation processes in the context of the present invention include, for example, simple distillation, rectification, absorption, fractional condensation, desorption, extraction, stripping or azeotropic rectification.

In contrast, a crystallizative removal is a "sharp" thermal separation process in that the composition of the crystals that form, from a thermodynamic point of view, is substantially independent of the composition of the liquid starting mixture.

While a high space-time yield is an advantage of "nonsharp" separation processes, a disadvantage thereof is that the separating action achieved thereby is comparatively limited. In contrast, "sharp" separation processes normally have comparatively modest space-time yields, whereas they exhibit a very high separation efficacy.

One example of a target product according to the present invention is acrylic acid. Acrylic acid and its salts and esters are an important commodity for preparation of polymers for a wide variety of different fields of use, such as adhesives, superabsorbents or binders. When it is synthesized, acrylic acid is typically not obtained as a pure product but as part of a substance mixture which, as well as the target compound desired in a high purity, also comprises unwanted constituents, for example solvents, starting compounds and by-products. Frequently, this substance mixture is a liquid.

Acrylic acid is obtainable, for example, by catalytic conversion of glycerol, propane, propene and/or acrolein. This involves diluting these starting compounds, preferably in the gas phase, generally with inert gases such as molecular nitrogen, $CO_2$ and/or water vapor, passing them over mixed transition metal oxide catalysts in a mixture with molecular oxygen at elevated temperatures and optionally elevated pressure, and converting them oxidatively to a product gas mixture comprising acrylic acid. By condensative and/or absorptive measures, the acrylic acid is then typically converted to the liquid (condensed) phase. There is already a basic separation here of the acrylic acid from the compounds that accompany it in the product gas mixture, but in no way quantitatively.

Using a wide variety of different combinations of "nonsharp" and "sharp" thermal separation processes, the acrylic acid is finally separated from the aforementioned liquid phases in high purity. The process of suspension crystallization is part of such process combinations in many cases. This involves cooling a mixture which comprises acrylic acid and is in the liquid state, which results in the formation of crystals of acrylic acid, in order to remove them virtually quantitatively from the mixture.

This exploits the fact that, as the crystals that form from acrylic acid grow, the constituents present alongside acrylic acid in the liquid mixture are frequently displaced from the crystal lattice and remain in the mother liquor.

Processes for suspension crystallization for crystallizative removal of acrylic acid are known, for example from DE 10 2007 043 748 A1, DE 10 2007 043 758 A1 or DE 10 2007 043 759 A1. As explained in general terms above, it is appropriate for application purposes to conduct this process with the aid of an indirect heat transferer (cooler or crystallizer) having a secondary space and at least one primary space.

However, a disadvantage of the apparatuses and processes known from the prior art has been found to be the tendency for crystallizative encrustations to form on the side of the dividing wall facing the secondary space, and the ability of this encrustation to adhere persistently to the dividing wall. The formation of such encrustations or adhering crystal layers is associated with a reduction in the heat transfer through the dividing wall. Thus, fewer crystals are formed per unit time and the throughput or purifying performance of the crystallizer consequently declines.

As well as the formation of encrustations on the heat exchanger surfaces of the crystallizer, encrustations also form in the feed and removal lines for the heat transfer medium and for the product removal. Such crystallizative encrustations, on attainment of a particular size, can spontaneously become detached as comparatively voluminous individual pieces and cause damage in a wide variety of ways.

For example, they can lead to damage to the pump used to convey the crystal suspension conducted out of the secondary space. In addition, individual pieces that become detached can damage mechanically moving parts, for example the wiper system within the crystallizer. Therefore, the layers of crystals formed on the dividing wall and in the lines have to be removed regularly.

In the removal of the layers of crystals, the feed of the liquid to be purified in the secondary space is typically stopped and warm heat carrier medium is introduced into the primary space of the cooling disks. The supply of heat results in detachment of the adhering layers of crystals. At the same time, some large fragments of layers of crystals become detached from the dividing plates or from the feed and removal lines for the heat transfer medium, and collect at the bottom of the secondary space on account of gravity. In order to avoid damage to the rotating wiper system in the course of melting in the first phase of the melting operation of the crystallizer by the large fragments of the detached layers of crystals, the wiper system is generally shut down in the course of melting. Since, after the wiper system has been shut down, the energy needed to melt the layers of crystals is then transferred essentially only through conduction of heat from the dividing plate through the liquid, the melting takes a comparatively long time.

In view of the disadvantages of the prior art, it is an object of the present invention to provide an apparatus and specify a process with which the crystal layers to be detached are dissolved very rapidly and no mechanical damage is caused to the crystallization unit.

The aforementioned object is achieved, in a first aspect of the invention, by an apparatus (1) for separation of a target product from a liquid phase P comprising the target product, comprising
  at least one primary space (3) for a heat transfer medium W,
  at least one first feed unit (5a) and one first removal unit (5b) for the heat transfer medium W,
  at least one secondary space (7) for the liquid phase P,
  at least one second feed unit (9) for the liquid phase P,
  at least one crystallization surface (13) which divides the primary space (3) and the secondary space (7),
  at least one second removal unit (15) for the target product and
  at least one application unit (11) for a liquid phase $P_0$ essentially directly to the crystallization surface (13) and/or the surfaces of lines that conduct the heat transfer medium W.

In a second aspect of the invention, the object is achieved by a process for separating a target product from a liquid phase P comprising the target product, comprising the process steps of:
a) feeding a cooled heat transfer medium W to a primary space (3) by means of a first feed unit (5a),
b) feeding the liquid phase P in a precooled state to a secondary space (7) by means of a second feed unit (9), in the course of which the saturation limit of the target product in the liquid phase P is exceeded as a result of heat transfer from the liquid phase P to the heat transfer medium W through a crystallization surface (13) disposed between the primary space (3) and the secondary space (7), resulting in deposition of the target product at the crystallization surface (13) as crystals A,
c) removing the crystals A from the crystallization surface (13) and removing them from the secondary space (7) by means of a second removal unit (15) and
d) removing the heated heat transfer medium W from the primary space (3) by means of a first removal unit (5b), with stoppage of the essentially continuous process steps a), b), c) and d) at predetermined time intervals and execution of process step e)
e) applying a warm liquid phase $P_0$ by means of an application unit (11) essentially directly to the crystallization surface (13) and/or the surfaces of lines conducting the heat transfer medium W.

With the apparatus (1) of the invention and the process of the invention, it is possible to overcome the disadvantages of the prior art and to gently and rapidly break down layers of crystals of the target product and encrustations. More particularly, it is possible with the present invention to distinctly reduce the shutdown time of the apparatus (1) of the invention compared to apparatuses of the same generic type, such that a more economically viable mode of operation is achieved.

If, in the description which follows, process features are also detailed in connection with the apparatus (1) of the invention, they preferably relate to the process of the invention, which is still to be defined in detail hereinafter. Equally, apparatus features which are mentioned in connection with the process of the invention relate preferably to the apparatus (1) of the invention.

The invention will now be described in detail.

The present invention firstly provides an apparatus (1) for separation of a target product from a liquid phase P comprising the target product. The apparatus (1) comprises at least one primary space (3) for a heat transfer medium W and at least one first feed unit (5a) and one first removal unit (5b) for the heat transfer medium W. In addition, the apparatus (1) has at least one secondary space (7) for the liquid phase P and at least one second feed unit (9) for the liquid phase P. The primary space (3) and the secondary space (7) are divided by at least one crystallization surface (13). In addition, the apparatus (1) comprises at least one second removal unit (15) for the target product. This apparatus (1) also has at least one application unit (11) for distributing the liquid phase P essentially directly to the crystallization surface (13) and/or the surfaces of lines that conduct the heat transfer medium W.

As outlined above, layers of crystals and encrustations of the target product can form on the crystallization surfaces (13) of an apparatus of the generic type. In order to be able to remove the layers of crystals and encrustations effectively and gently, the apparatus of the invention comprises at least one application unit (11), by means of which the liquid phase P in the at least warmed state can be applied essentially directly to the crystallization surface (13) and/or the surfaces of lines that conduct the heat transfer medium W. As a result, layers of crystals and encrustations that form can be dissolved or thawed without detachment of any large pieces of crystals or, if they do form, without such pieces leading to any damage to parts that are moved mechanically during the melting operation.

In a development of the apparatus (1) of the invention, the application unit (11) comprises a pipeline system having nozzles for distributing the liquid phase $P_0$ over the crystallization surface (13) covered with crystal layers or encrustations and/or the surfaces of lines that conduct the heat transfer medium W. It is advantageous when the liquid phase P supplied, before being distributed, is heated to a temperature above the crystallization or saturation temperature. These design features of the application unit (11) especially assure application of the liquid phase P in a homogeneous distribution over the particular crystallization surface (13) and/or surfaces of lines that conduct the heat transfer medium W, and hence homogeneous dissolution or thawing away.

In one embodiment of the invention, the liquid phase $P_0$ may include the liquid phase P or a liquid phase $P_1$ comprising at least one solvent. The solvent is preferably water.

In order to be able to conduct the removal of the crystal layers or encrustations by melting or dissolution without contaminating the liquid phase P, the introduction unit is preferably charged with the liquid phase P, with adjustment of liquid phase P supplied via an upstream liquid phase P heat exchanger (23) to a temperature above the melting point of the crystal layers or encrustations. If here the liquid phase P for the application unit (11) is removed from the secondary space (7) by means of a pump (25), and returned to the application unit (11) through feed unit (21), for example, the circulation that this creates causes very effective removal of the crystal layers or encrustations by melting or dissolution.

It has additionally been found to be advantageous for quicker removal of the crystal layers or encrustations by melting or dissolution when the apparatus (1) further comprises a heat exchanger (19) for the heat transfer medium W, arranged upstream of the first feed unit (5a). It is thus possible to preheat the heat transfer medium W which flows through the particular primary space (3).

More preferably, the apparatus (1) is configured as a cooling disk crystallizer.

The present invention secondly provides a process for separating a target product from a liquid phase P comprising the target product. This process can especially be executed by means of an apparatus (1) of the invention, as described above.

In a process step a), a cooled heat transfer medium W is fed to a primary space (3) by means of a first feed unit (5a). In a process step b), the liquid phase P is then fed in a precooled state to a secondary space (7) by means of a second feed unit (9), in the course of which the saturation limit of the target product in the liquid phase P is exceeded as a result of heat transfer from the liquid phase P to the heat transfer medium W through a crystallization surface (13) disposed between the primary space (3) and the secondary space (7), resulting in deposition of the target product at the crystallization surface (13) as crystals A.

In a process step c), the crystals A are removed from the crystallization surface (13) and removed from the secondary space (7) by means of a second removal unit (15). At the same time or at another time, in step d), the heated heat transfer medium W is removed from the primary space (3) by means of a first removal unit (5b).

At predetermined time intervals, the essentially continuously executed process steps a), b), c) and d) are then stopped and process step e) is executed, in which, finally, a warm liquid phase $P_0$ is applied by means of an application unit (11) essentially directly to the crystallization surface (13) and/or the surfaces of lines conducting the heat transfer medium W.

"Warm liquid phase $P_0$" is understood to mean a liquid phase having a temperature above the melting point of the crystal layers or encrustations.

As already explained above for the apparatus (1), it enables the application of warm liquid phase P by means of the inventive application unit (11), crystal layers or encrustations that arise to be degraded gently and rapidly, without pieces thereof becoming detached and causing mechanical damage to parts of the apparatus (1). By applying the warm liquid phase P essentially directly to the crystallization surface (13) and/or the surfaces of lines that conduct the heat transfer medium W, it is directed in a controlled manner onto the areas and surfaces in question, in order to bring about the desired effect of the invention of removing crystal layers or encrustations by melting or dissolving.

In a development of the process of the invention, in parallel to process step e), the following process steps are executed at least temporarily: aa) feeding a heated heat transfer medium W to the primary space (3) by means of the first feed unit (5a) and/or dd) removing the cooled heat transfer medium W from the primary space (3) by means of a first removal unit (5b). This promotes the removal of crystal layers or encrustations from the primary space (5) (i.e. from the interior of the cooling disk (103)) by melting or dissolution which has been brought about from the secondary space (7). The same applies to the lines within which the heat transfer medium W flows.

Alternatively or additionally, in parallel to process step e), the following process step may be executed at least temporarily: f) circulating the liquid phase P from the secondary space (7) by means of a second heat exchanger (23) and feeding the heated liquid phase P to the application unit (11). This measure too further promotes the removal of crystal layers or encrustations by melting or dissolution.

In a preferred embodiment, the liquid phase P is a product mixture comprising acrylic acid, preferably having a concentration of >80% by weight, and the crystals A are pure acrylic acid, preferably having a proportion of >99% by weight.

Further aims, features, advantages and possible uses are apparent from the description of working examples of the present invention that follows, with reference to the figures. All the features described and/or shown pictorially, alone or in any combination, form the subject matter of the present invention, even with no regard to the way in which they are recited in the claims or the dependency references thereof.

Figure 2:
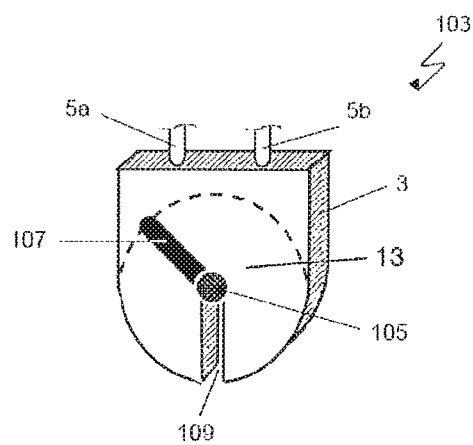

The figures show:

FIG. 1 a schematic diagram of a cooling disk crystallizer 1 in one embodiment of the present invention and FIG. 2 a schematic cross-sectional diagram of a cooling disk 103 in one embodiment of the present invention.

FIG. 1 shows a schematic diagram of a cooling disk crystallizer 1 as a preferred embodiment of the apparatus 1 of the invention. This is a stirred apparatus in a horizontal arrangement. As can be inferred from FIG. 1, it comprises, as main constituents, a trough-shaped housing 101 and the cooling disks 103 suspended vertically from the top of the housing 101, which are arranged at right angles to the longitudinal axis of the apparatus 1 and parallel to one another. A horizontal shaft 105 with radial wipers 107 runs along the longitudinal axis through the trough-shaped housing 101, which is not shown explicitly in FIG. 1. The cooling disks 103 have, in the lower half thereof, a cutout 109 in order to be able to push them over the shaft 105 (cf. FIG. 2).

The interior of the trough-shaped housing 101 essentially forms the secondary space 7 in which the liquid phase P is accommodated, the latter being supplied essentially continuously by the second feed unit 9. On the opposite side of the apparatus 1 is disposed a second removal unit 15 for the target product. Here, essentially a suspension S of the crystallized target product is drawn off. It is likewise possible to provide a third removal unit 17 for by-products N (not shown here).

By means of the cooling disks 103, the liquid phase P supplied is cooled indirectly. The liquid phase P and the heat transfer medium W which acts as coolant in this mode of operation are conducted through the apparatus 1 in countercurrent. The cooling disks 103 bring about substantial division of the working volume, such that only slight axial backmixing exists and corresponding temperatures and (solids) concentration profiles can be established. The wipers 107 which rotate slowly with the shaft 105 are supposed to keep the cooling disks 103 substantially free of crystal layers or fouling, and hence enable the continuous removal of heat and the continuous operation of the cooling disk crystallizer 1. As described above, however, there are regions on the cooling disks 103 that are not reached by the wipers 107, such that crystal layers or fouling can form there. These crystal layers or this fouling can likewise form on lines through which the heat transfer medium W is conducted into the secondary space 7 and through it between the cooling disks 103.

Above the cooling disks 103 are arranged a plurality of application units 11, in the preferred case one or more application units 11 for each cooling disk 103, through which liquid phase P is applied to the cooling disks 103, especially to the crystallization surfaces 13, and the surfaces of the lines that conduct the heat transfer medium W. The application units 11 are generally designed as a pipeline system with nozzles.

In the regular operation of the cooling disk crystallizer 1, precooled liquid phase P is supplied through the second feed unit 9, while cold or cooled heat transfer medium W is passed in countercurrent through the cooling disks 103, in order to achieve optimal deposition of the target product as crystals. This will be explained further hereinafter.

In the regenerative operation of the cooling disk crystallizer 1, in contrast, the feed of precooled liquid phase P is stopped and, instead, the application unit 11 is preferably supplied with preheated liquid phase $P_0$, in order to accelerate the removal of crystal layers or encrustations on the crystallization surfaces 13 by melting or thawing. The second heat exchanger 23 can serve for heating. The liquid phase $P_0$ used for this purpose can especially be drawn off from the secondary space 7 in the form of liquid phase P, preferably via an outlet not shown in the figures, which is preferably within the upper section of the secondary space 7, in order to supply a very substantially solids-free liquid phase P to a circulation pump 25.

In a simplified embodiment, the application unit 11 can also be supplied with the precooled liquid phase P from the second feed unit 9, but in that case the removal by melting or dissolution takes longer.

For further promotion, the heat transfer medium W is additionally converted from the cold state to a heated state, for example with the first heat exchanger 19, such that the removal by melting or dissolution is accelerated from the inside by heating of the cooling disks and lines.

The cooling disk 103 shown in FIG. 2 has a primary space 3 through which the heat transfer medium W flows, the latter being supplied via a first feed unit 5a and removed via a first removal unit 5b. This primary space 3 is defined here essentially by two crystallization surfaces 13 and is concluded at the top and bottom in a suitable manner. The cooling disk 103 also has a space to accommodate a shaft 105, the rotating motion of which slowly rotates wipers 107.

The individual primary spaces 3 (in the individual cooling disks 103) are connected to one another, such that the cooled heat transfer medium W preferably flows in countercurrent to the precooled liquid phase P. In this case, the cooling disks 103 can be divided into two parallel runs, in order to assure a good internal heat transfer coefficient, i.e. a sufficiently high flow rate of the heat transfer medium W through the primary spaces 5 with simultaneous limitation of the cumulative pressure drop over the cooling disks 103. In addition, good integratability of the pipework in the apparatus 1 is enabled.

In a specific embodiment, the transfer of heat from the acrylic acid-comprising liquid phase P which is supplied to the secondary space 7 (and generally flows through it) through the crystallization surface 13 which separates the secondary space 7 and the at least one primary space 3 from one another to a cold or cooled heat transfer medium W which flows within the at least one primary space 3 cools the liquid phase P down until its saturation limit with acrylic acid is exceeded and the liquid phase P counteracts the saturation by forming (i.e. depositing) crystals A formed from acrylic acid (as target product).

Once the desired crystallization level has been attained (the term "crystallization level" here means the mass fraction or else proportion by mass of the fine crystals present in the resulting suspension of crystals of acrylic acid in remaining mother liquor (remaining in liquid form) in the total mass of the crystal suspension), the suspension S is conducted out of the secondary space 7 via the second removal unit 15. By removing the acrylic acid crystals A formed from the mother liquor, it is possible to isolate the acrylic acid from the suspension S in appropriate purity.

The term "mother liquor" is understood such that it includes both melts (in these, a proportion by weight of ≥50% by weight is accounted for by the acrylic acid) composed of acrylic acid and impurities, and solutions of acrylic acid and any impurities that accompany it in solvents or in solvent mixtures (in these, a proportion by weight of ≥50% by weight is accounted for by the acrylic acid), with the proviso that the acrylic acid crystallizes out when they are cooled (i.e. in the course of cooling of the mother liquor).

In a development of the cooling disk 103, as installable with preference in the apparatus 1 from FIG. 1, this cooling disk 103 has a primary space 5 divided into two separate flow spaces. In regular operation, cold heat transfer medium W flows through the main flow space, which is provided with a series of guide plates and baffle plates, in order to obtain a good flow pathway, i.e. good heat transfer combined with low pressure drop. The secondary flow space consists of a tube placed around the periphery of the main flow space, through which warm heat transfer medium W flows. In this way, to a certain degree, encrustations on the unwiped surfaces of the cooling disk 103 can be at least reduced. Cold and warm heat transfer medium W are each conducted into and out of the cooling disk 103 vertically from the top.

In a cooling disk crystallizer 1 on the industrial scale, in one embodiment of the invention, 24 cooling disks 103 are provided. The main dimensions of the cooling disk crystallizer 1 are length 9.4 m, width 3.7 m and height about 4 m, with an active suspension volume of about 76 m³. Together with the support devices for the external shaft bearing and the drive, the total length of the cooling disk crystallizer 1 amounts to about 12 m.

The invention claimed is:

1. An apparatus (1) for separation of a target product from a liquid phase P comprising the target product, comprising
   a plurality of primary spaces (3) for a heat transfer medium W and a plurality of cooling disks (103), each primary space located within each cooling disk,
   lines having surfaces which conduct the heat transfer medium W,
   a first feed unit (5a) and a first removal unit (5b) for the heat transfer medium W,
   a plurality of secondary spaces (7) for the liquid phase P,
   a second feed unit (9) for the liquid phase P,
   a plurality of crystallization surfaces (13), each crystallization surface located within each cooling disk, and each crystallization surface divides each primary space from the secondary spaces (7), a second removal unit (15) for the target product, and a plurality of application units (11) for distributing a liquid phase $P_0$ essentially directly to the crystallization surfaces (13) and the surfaces of lines that conduct the heat transfer medium W, wherein one or more of the plurality of application units (11) are arranged for each cooling disk.

2. The apparatus (1) according to claim 1, wherein each application unit (11) comprises a pipeline system having nozzles for distributing the liquid phase $P_0$ over each crystallization surface (13) of each cooling disk (103) and the surfaces of lines that conduct the heat transfer medium W.

3. The apparatus (1) according to claim 1, wherein the liquid phase $P_0$ comprises at least one of the liquid phase P and a liquid phase $P_1$ comprising a solvent.

4. The apparatus (1) according to claim 1, further comprising a heat exchanger (19) for the heat transfer medium W, arranged upstream of the first feed unit (5*a*).

5. The apparatus (1) according to claim 1, wherein the apparatus (1) is a cooling disk crystallizer.

\* \* \* \* \*